US008547094B2

(12) United States Patent
Jellus et al.

(10) Patent No.: US 8,547,094 B2
(45) Date of Patent: Oct. 1, 2013

(54) METHOD FOR DETERMINING AN ATTENUATION MAP FOR USE WITH POSITRON EMISSION TOMOGRAPHY AND MAGNETIC RESONANCE MAGNETIC FIELD HOMOGENEITY FROM A SINGLE THREE DIMENSIONAL GRADIENT ECHO SEQUENCE

(75) Inventors: Vladimir Jellus, Erlangen (DE); Michael Szimtenings, Bonn (DE)

(73) Assignee: Siemens Aktiengesellschaft, Munich (DE)

( * ) Notice: Subject to any disclaimer, the term of this patent is extended or adjusted under 35 U.S.C. 154(b) by 898 days.

(21) Appl. No.: 12/461,902

(22) Filed: Aug. 27, 2009

(65) Prior Publication Data

US 2010/0052674 A1 Mar. 4, 2010

(30) Foreign Application Priority Data

Aug. 28, 2008 (DE) .......................... 10 2008 044 844

(51) Int. Cl.
*G01R 33/48* (2006.01)

(52) U.S. Cl.
USPC .......................................... 324/307; 324/309

(58) Field of Classification Search
USPC . 324/300–322; 600/407–435; 382/128–131; 514/339
See application file for complete search history.

(56) References Cited

U.S. PATENT DOCUMENTS

| 5,070,876 | A | * | 12/1991 | Wright ........................... 600/419 |
| 6,091,243 | A | * | 7/2000 | Xiang et al. ................... 324/307 |
| 6,263,228 | B1 | | 7/2001 | Kramer | |

(Continued)

FOREIGN PATENT DOCUMENTS

| EP | 1380257 A1 | 1/2004 |
| WO | WO 2005055136 A2 | 6/2005 |

OTHER PUBLICATIONS

Bernard D. Coombs et al. "Two-Point Dixon Technique for Water-Fat Signal Decomposition with Bo Inhomogeneity correction"; Magn. Reson. Med. 1997, vol. 38, p. 884-889; Others; 1997.
German Office Action dated Nov. 2, 2009.

*Primary Examiner* — Melissa Koval
*Assistant Examiner* — Tiffany Fetzner
(74) *Attorney, Agent, or Firm* — Harness, Dickey & Pierce, P.L.C.

(57) ABSTRACT

A method is disclosed for determining an attenuation map for use in positron emission tomography and for the use of homogeneity information relating to the magnetic resonance magnetic field, in particular for the purpose of determining shim settings, within the scope of a single magnetic resonance image recording. In at least one embodiment of the method, a first and a second image data record are firstly recorded with a three-dimensional gradient echo sequence during a first and a second echo time, respectively, with the phase difference between the water and the fat signal amounting to zero during the first echo time and amounting to 180 degrees during the second echo time. The attenuation map is determined from fat/water ratios obtained from the image data records by way of a Dixon technology, in particular a 2-point Dixon technology. In at least one embodiment, all voxels with a signal intensity below a first threshold value are excluded at least for the second image data record by using a mask and only the non excluded voxels of the first and second image data record are taken into consideration in order to determine the homogeneity information from the phase differences of adjacent voxels.

20 Claims, 2 Drawing Sheets

(56) References Cited

U.S. PATENT DOCUMENTS

| | | |
|---|---|---|
| 6,373,249 B1 | 4/2002 | Kwok et al. |
| 7,179,821 B2 * | 2/2007 | Smith et al. ................... 514/339 |
| 7,233,143 B2 | 6/2007 | Duerk |
| 7,609,060 B2 * | 10/2009 | Hetherington et al. ....... 324/307 |
| 7,787,671 B2 * | 8/2010 | De Leon et al. .............. 382/128 |
| 8,131,043 B2 * | 3/2012 | Binkley et al. ................ 382/131 |
| 8,280,136 B2 * | 10/2012 | Gotardo et al. ............... 382/131 |
| 8,378,682 B2 * | 2/2013 | Subbarao ...................... 324/318 |
| 2003/0062900 A1 * | 4/2003 | Kiefer et al. .................. 324/320 |
| 2006/0025673 A1 * | 2/2006 | De Leon et al. .............. 600/410 |
| 2008/0253638 A1 * | 10/2008 | Binkley et al. ................ 382/131 |
| 2008/0258725 A1 * | 10/2008 | Hetherington et al. ....... 324/307 |
| 2008/0260230 A1 * | 10/2008 | Gotardo et al. ............... 382/131 |
| 2010/0052674 A1 * | 3/2010 | Jellus et al. ................... 324/309 |
| 2011/0044524 A1 * | 2/2011 | Wang et al. ................... 382/131 |
| 2011/0115485 A1 * | 5/2011 | Subbarao ...................... 324/309 |

* cited by examiner

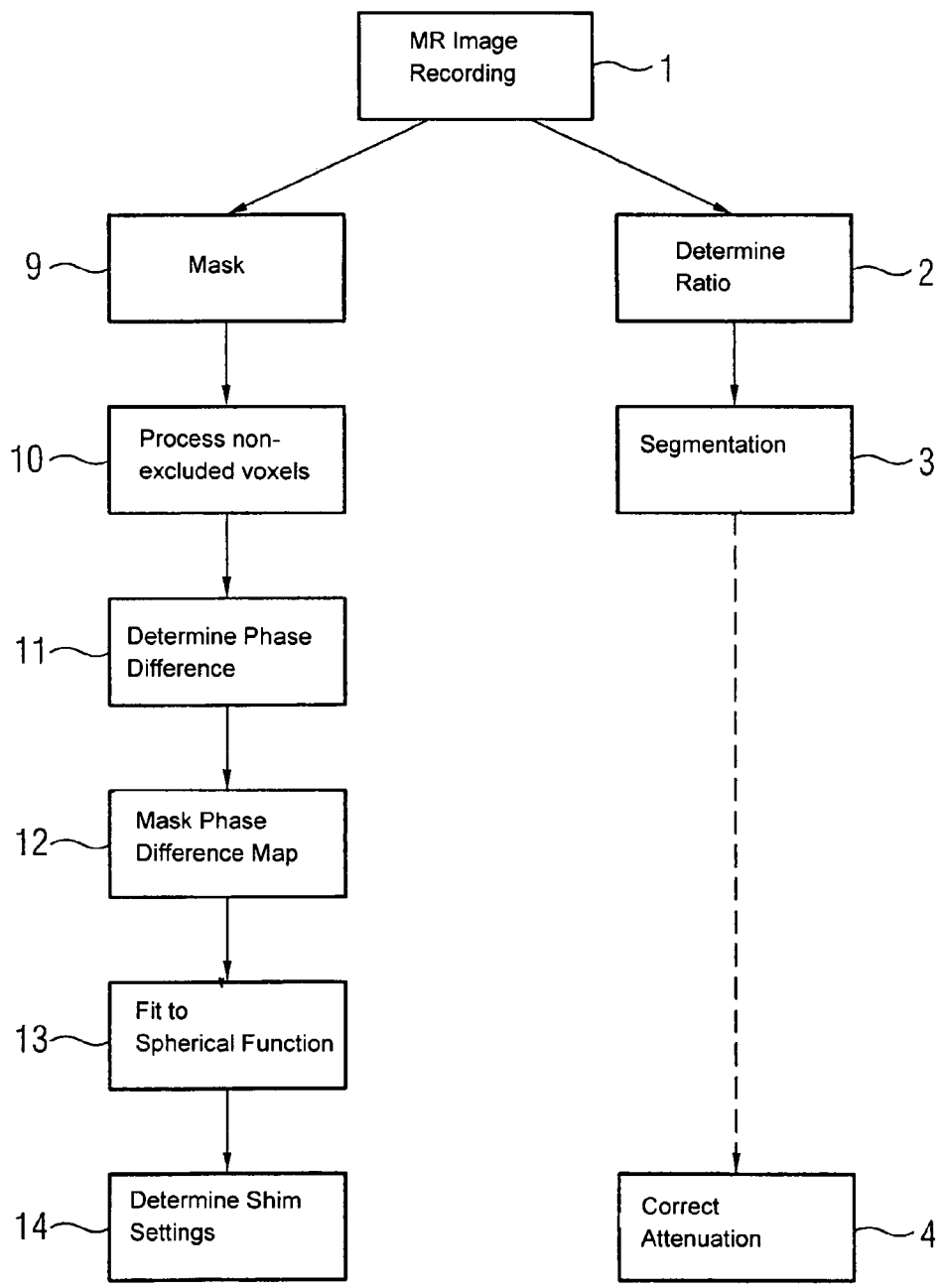

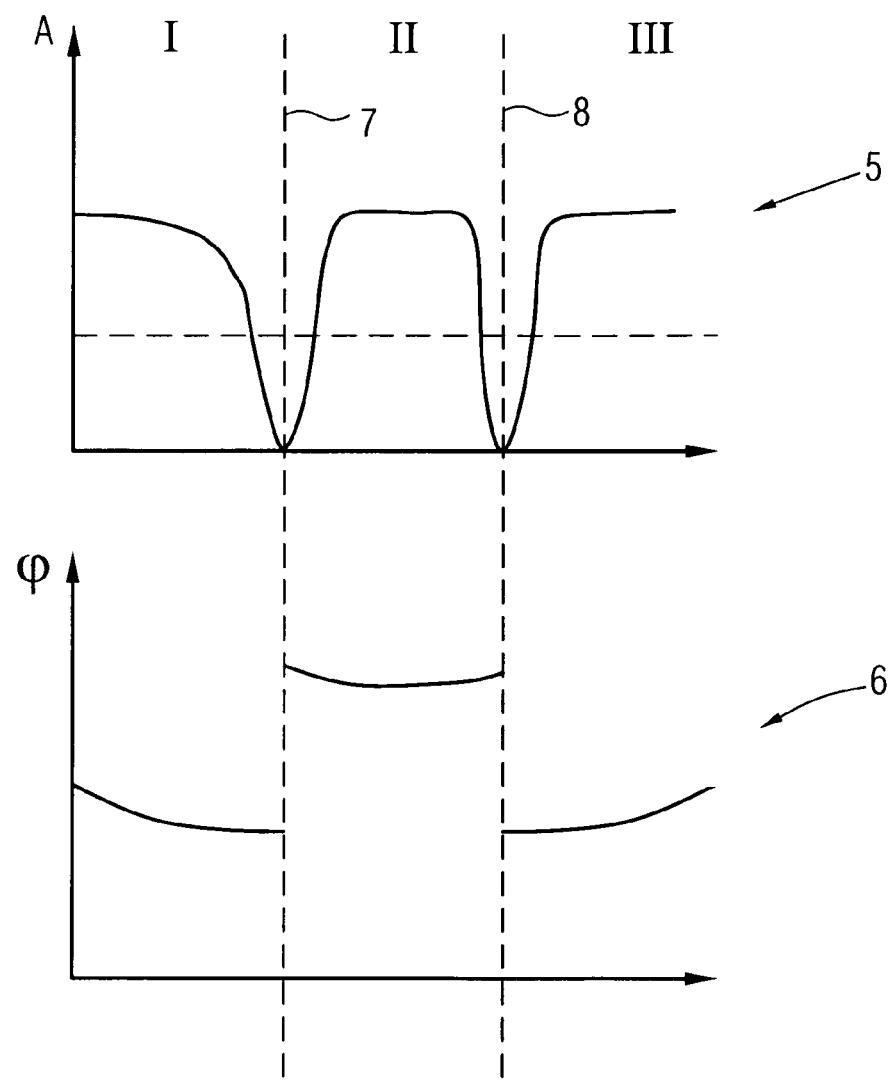

METHOD FOR DETERMINING AN ATTENUATION MAP FOR USE WITH POSITRON EMISSION TOMOGRAPHY AND MAGNETIC RESONANCE MAGNETIC FIELD HOMOGENEITY FROM A SINGLE THREE DIMENSIONAL GRADIENT ECHO SEQUENCE

PRIORITY STATEMENT

The present application hereby claims priority under 35 U.S.C. §119 on German patent application number DE 10 2008 044 844.3 filed Aug. 28, 2008, the entire contents of which are hereby incorporated herein by reference.

FIELD

At least one embodiment of the invention generally relates to a method for determining an attenuation map for use in positron emission tomography and for the use of homogeneity information relating to the magnetic resonance magnetic field, in particular for the purpose of determining shim settings.

BACKGROUND

Combined magnetic resonance positron emission tomography devices (MR-PET devices), as were recently proposed, allow for a combination of two imaging methods, which interact particularly well. Within the scope of combined MR-PET examinations, some pre-measurements of magnetic resonance images are however generally necessary.

On the one hand, a locally-resolved knowledge of the attenuation values of the tissue of the current patient, the so-called attenuation map, is needed in order to evaluate the results of a PET measurement. This information allows the PET data to be corrected accordingly during the evaluation. It is therefore known to produce an MR image recording, from which different tissue classes can be identified.

A known method for this is the so-called Dixon method for separating water and fat. This method relates to the small difference in the Lamor frequency of protons bound in fat and water. To this effect, this frequency difference is noticeable such that the phases of protons in the fat and in the water diverge. A distinction is made here in particular between the state in which the fat and water magnetization are in phase ("in-phase-condition") and the state in which the phase difference amounts to exactly 180° ("opposed-phase-condition"). While in the first instance the signals mutually intensify within a voxel, in the second instance an attenuation takes place. With the Dixon methods, two echoes are now recorded after a single excitation, namely an image, in which the phase difference between the water and the fat signal amounts to zero and an additional image, wherein the phase difference between the water and the fat signal amounts to 180°. One image therefore corresponds to the addition of water and fat signals, the other image corresponds to a subtraction of water and fat signals. The fat/water ratio within a voxel can however be determined therefrom. This information is used as a basis to calculate the attenuation map.

A second premeasurement which is relevant in respect of the actual MR examination and has to be implemented is a measurement to determine the shim settings. A body introduced into the B0 field of a magnetic resonance facility interferes with the homogeneity of this field. It is therefore necessary to determine shim correction terms in order to reproduce homogeneity. It is known to record two data records within the scope of an MR image recording, in which water and fat are in the same phase. The difference in the phases of adjacent voxels is directly connected to the field differences and can then be used to determine the deviations from the homogeneity. Corresponding shim settings are in turn derived herefrom, for instance shim currents or shim coils.

The implementation of these two measurements is time-consuming and puts additional stress on the patient who is not permitted to move at all during the examination. A renewed double MR image recording must also take place for each position of the patient positioning couch.

SUMMARY

In at least one embodiment of the invention, a method is specified, with which a more rapid and simpler determination of the attenuation map and the shim settings is possible.

In order to solve or at least improve upon this problem, provision is made in accordance with at least one embodiment of the invention for a method for determining an attenuation map for use in positron emission tomography and for the use of homogeneity information relating to the magnetic resonance magnetic field, in particular for the purpose of determining shim settings, within the scope of a single magnetic resonance image recording, with a first and a second image data record being firstly recorded with a three-dimensional gradient echo sequence during a first and a second echo time, respectively, with the phase difference between the water and the fat signal amounting to zero during the first echo time and amounting to 180° degrees during the second echo time, the attenuation map being determined from fat/water ratios obtained from the image data records by way of a Dixon technology, in particular a 2-point Dixon technology, all voxels with a signal intensity below a first threshold value being excluded at least for the second image data record by using a mask, and only the non-excluded voxels of the first and second image data record being taken into account in order to determine the homogeneity information from the phase differences of adjacent voxels.

It is thus possible with the aid of the method according to at least one embodiment of the invention to obtain homogeneity information relating to the magnetic resonance field as well as an attenuation map for the correction of PET data within the scope of only one single magnetic resonance image recording. To this end, only two image data records, namely one during a first and one during a second echo time, need to be recorded as a reaction to a single excitation. The echo times are selected here such that the phase difference between the water and the fat signals amounts once to zero and once to 180°, in other words the underlying image data records which are needed to determine the fat/water ratio are obtained. In accordance with the invention, it is however also possible, despite the images having been recorded during different phase differences between the water and the fat signal, to consequently reliably perform a determination of the homogeneity information for the purpose of determining shim settings. To this end, a mask is provided in accordance with the invention which extracts all the voxels from the examination which are not able to provide any reliable phase information.

As already mentioned, the signal in the second image data record is attenuated in voxels with fat and water parts. At the point at which the water parts and the fat parts correspond exactly, no signal is consequently measured, furthermore a phase jump about 180° is observed during the transition through this point. The transition regions in which fat and water parts correspond quite accurately, are thus critical. Allowance is made for the mask applied to the second data image record, which excludes all voxels with a signal intensity below a threshold value, from the additional examination within the scope of determining the homogeneity information. The extent of the threshold value can be selected here as a function of the scale such that sufficient non-excluded points remain in order to reliably determine the homogeneity information and only the regions in which the signal (and thus also the signal-to-noise ratio) is too low are actually excluded in order to use its information. In addition to the cited transition regions in which fat and water parts almost or exactly correspond, empty regions which are not occupied by an object, for instance outside a patient body, are thus also excluded as they only supply one noise signal.

It was therefore established within the scope of at least one embodiment of the present invention that the two image data records needed for a Dixon technology can also be used to determine the homogeneity information, if the non-evaluable voxels which can be easily identified in the second image data record are removed from the examination. The homogeneity information which results from the phase differences of adjacent voxels can subsequently be determined, as known, from the remaining non-excluded voxels of the first and second image data record.

Advantageously, one single MR image recording is sufficient in the case of the method according to at least one embodiment of the invention, in order to obtain both types of information. This saves on examination time as fewer scans are needed. This is enabled by a single three-dimensional MR image recording with two image data records, namely a first "in-phase" image data record and a second "opposed-phase" image data record being used, which is then used simultaneously to calculate an attenuation map and to determine the homogeneity information, in particular the shim settings. The 2-point Dixon technology is advantageously combined with the shim calculation.

Provision can be made in an additional expedient embodiment for the mask to also be applied to the first image data record. In this way more reliable voxels which can be evaluated with more difficulty, in which no object is present, or voxels with measurement errors can be ruled out.

In an advantageous embodiment of the method according to the invention for the non-excluded voxels, a third image data record can be calculated by multiplying the signal intensities of the first or second image data records with the complexly conjugated of the signal intensities of the second or first image data record in order to determine the homogeneity information. This is advantageous in that phase variations, which are caused by the high frequency coils, are removed.

For at least one image data record, in particular the third image data record, in which phase variations were eliminated by the high frequency coil, the phase differences of adjacent voxels can be determined as phase difference maps. In a voxel dominated by fat or water, the spatial phase difference is not influenced by the fact that both echoes, in other words both image data records, do not fulfill the "in-phase condition", as already mentioned above. The voxels, in which fat and water parts, in other words fat and water signals, are of similar sizes, are already excluded by the mask however. A reliable phase difference map is generated here.

Provision can be expediently made in order to determine spherical function coefficients as homogeneity information for the phase difference map to be fitted to spherical function phase difference maps. Other possibilities which enable the determination of the spherical function coefficients are naturally also conceivable and are essentially known in the prior art.

Phase differences between adjacent voxels that are below a second threshold value which is less than 180° can preferably be taken into account when determining the homogeneity information. One example of the second threshold value would be 160° for instance. All regions, in which the phase difference of "phase-wraps" is ambiguous are sorted in this way. It is however also possible to largely eliminate this using techniques for correcting the "phase-wraps", nevertheless these techniques are very error-prone and could thus result in unusable results. Furthermore, the use of the second threshold value particularly advantageously allows for artificially high phase jumps to be eliminated on fat-water limit surfaces, as mentioned already above, which could similarly result in incorrect results.

As already mentioned, shim settings can be determined from the homogeneity information, whereupon, in the case of additional magnetic resonance image recordings of the examination, a shim facility is controlled according to the shim settings. This setting, like the whole method according to at least one embodiment of the invention, then takes place completely automatically so that the shim settings for a certain position of the patient and/or the patient support couch can be maintained during the whole MR-PET examination.

Provision can be expediently made for additional tissue types to be segmented within the scope of determining the attenuation map, with, in particular, a tissue atlas being taken into consideration as previous knowledge. If the fat/water ratios of the different voxels are firstly known, segmentation methods can be applied in order to spatially localize certain tissue types, the attenuation value of which is known. A tissue atlas can be considered here particularly advantageously, this means that background information is used in order to locate certain tissue regions and subsequently to segment them. If the space in which the tissue is located is known, the attenuation map can be created which is then used to correct PET data within the scope of the subsequently occurring MT-PET examination.

BRIEF DESCRIPTION OF THE DRAWINGS

Further advantages and details of the present invention result from the example embodiments described below as well as with reference to the drawings, in which;

FIG. 1 shows a flowchart of the method according to an embodiment of the invention, and FIG. 2 shows an illustration of possible signal courses in the second image data record.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows a flow chart of the method according to an embodiment of the invention. It can take place in particular completely automatically, for instance with the aid of a computing facility of a combined magnetic resonance positron emission tomography device.

An MR image recording is firstly implemented in a step 1. To this end, a three-dimensional gradient echo sequence is used, with a first and a second data image record being recorded during different echo times in each instance, namely a first and second echo time, after a single excitation. The first image data record is recorded if the phase difference between the water and the fat signal amounts to zero ("in-phase condition"). The second echo time indicates that the phase difference between the water and the fat signal amounts precisely to 180° ("opposed-phase condition").

An attenuation map as well as shim settings should now also be determined from these two image data records of the one magnetic resonance image recording. This can, as indicated in FIG. 1, take place in parallel, but is also possible consecutively. The computing facility of the combined MR-PET device can also be embodied in order to implement the evaluation steps.

In order to determine the attenuation map from the image data records, the attenuation map basically already being known and is as a result only to be outlined in brief here, the fat/water ratio is initially determined for each voxel in step 2 with the aid of the 2-point Dixon technology. This is possible since an image finally reproduces the total of the water and fat signal (the first image data record), the other image (the second image data record), the difference thereof, since when the "opposed-phase condition" exists, the signals attenuate mutually.

In step 3, a segmentation of different tissue types is then performed on the basis of the fat/water ratios using a tissue atlas, the attenuation coefficients of which are known. The attenuation map can thus be determined. This is used in the further course of the examination, step 4, in order to correct the attenuation of recorded PET data.

It is however also possible with the method according to an embodiment of the invention to determine homogeneity information relating to the magnetic resonance magnetic field and shim settings therefrom. In voxels which are dominated by the fat signal or the water signal (subsequently referred to as "fat-dominated" or "water-dominated") the spatial phase difference is not influenced such that both image data records were recorded in the case of different phase differences between fat and water.

It is therefore only the transition regions which are then problematic, as shown in more detail by FIG. 2. Example graphs 5 and 6 are shown there, which indicate a detail of a second image data record from an arbitrary direction. In this way, graph 5 shows the amplitude of the measuring signal against the local coordinate, graph 6 shows the phase of the measuring signal against the local coordinate.

While the regions I and III are water-dominated, region II is fat-dominated. It is apparent from graph 5 that the amplitude drops to very low values in the limit ranges. This results from the already mentioned effect such that the fat signal and the water signal attenuate in the second image data record due to the "opposed-phase condition". If the two signals are equally large, in other words that fat and water parts are comparable, no signal can thus be measured. A phase jump of 180° occurs at these points 7, 8 at the transition from the water-dominated regions I, III to the fat-dominated region II, as apparent from graph 6. The environment around points 7, 8 (which in the object itself are naturally limit surfaces when viewed three-dimensionally) cannot be evaluated expediently in order to determine the homogeneity information due to its low amplitude, in other words the low signal intensity which specifies a high signal-to-noise ratio and to the phase jump.

In step 9 (FIG. 1), a mask is now therefore placed over the first and the second image data record, which excludes all voxels, the signal intensity of which is lower than a first threshold value, from the further examination within the scope of determining the homogeneity information. It is therefore not only the regions which indicate an excessive reduction in the signal intensity in the second image data record as a result of mutual attenuation of the water and fat signals that are removed from the examination but also the voxels that do not contain any part of the object, in other words only noise.

In a step 10, the non-excluded voxels are then further processed such that a third data record is determined, with the complex signal intensities (including amplitude and phase) of the first image data record being multiplied voxel by voxel with the complexly conjugated of the signal intensities of the second image data record. This determines the difference in phases between the first and the second image data record so that phase variations due to high frequency coils are removed.

A phase difference map is then determined in a step 11, the phase difference map specifying the phase differences between adjacent voxels and forming the basis of the determination of the homogeneity information. This map can be defined in the following way for instance:

$$d4(x,y,z,1)=argv(d3(x,y,z)*conj(d3(x+1,y,z)))$$

$$d4(x,y,z,2)=argv(d3(x,y,z)*conj(d3(x,y+1,z)))$$

$$d4(x,y,z,3)=argv(d3(x,y,z)*conj(d3(x,y,z+1))),$$

whereby x, y and z indicate the voxels in the spatial directions, d3 indicates the signal intensity of the third image data record, d4 indicates the phase difference, and conj indicates the complex conjugation and argv indicates the selection of the phase of a complex number.

A further mask is then applied to the phase difference map in step 12. All phase differences which are greater than a second threshold value, here 160°, are namely not noted again. In this way it is not only regions with ambiguous phase differences which are ruled out due to "phase-wraps", but artificially high phase jumps on the fat/water boundary surface are also eliminated. In the case of significant jumps for instance, voxels of lower amplitude need not necessarily lie between water or fat-dominated regions.

In step 13, spherical function coefficients are to be determined from the remaining phase differences of the phase difference card as homogeneity information, said spherical function coefficients immediately specifying the inhomogeneity of the magnetic resonance magnetic field. To this end, provision is made for the phase difference map to be fitted to spherical function phase difference maps. Other techniques of matching the phase difference map to corresponding phase differences described by spherical functions are naturally also possible here.

The shim settings are finally determined in step 14 from the determined homogeneity information and are used to adjust a corresponding shim facility for the actual MR-PET examination which now follows.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDS; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining an attenuation map for use in positron emission tomography (PET) and for determining homogeneity information relating to the magnetic resonance (MR) magnetic field within the framework of a single magnetic resonance image recording, the method comprising:
   executing, by a MR-PET device, a single three-dimensional MR gradient echo sequence having a first echo time and a second echo time during a single excitation;
   recording, by the MR-PET device, a first and a second image data record of the single three-dimensional MR gradient echo sequence during the first and the second echo time, respectively, a phase difference between a water and a fat signal amounting to zero during the first echo time and amounting to 180 degrees during the second echo time; and
   determining, by the MR-PET device, the attenuation map for use in correcting PET data from fat/water ratios obtained from the first and second image data records by way of Dixon technology;
   excluding all voxels with a signal intensity below a first threshold value from at least the second image data record by using a mask; and
   determining, by the MR-PET device, homogeneity information from phase differences of adjacent voxels, taking into account only non-excluded voxels of the first and second image data records whereby both the homogeneity information and the attenuation map are determined from a single three-dimensional gradient echo sequence.

2. The method as claimed in claim 1, wherein the mask is also applied to the first image data record.

3. The method as claimed in claim 1, further comprising: calculating a third image data record for the non-excluded voxels by multiplying signal intensities of the first or second image data records with the complex conjugates signal intensities of the other second or first image data record.

4. The method as claimed in claim 1, wherein phase differences of adjacent voxels are determined as a phase difference map for at least one of the first and second image data records.

5. The method as claimed in claim 4, wherein the phase difference map is fitted to spherical function phase difference maps.

6. The method as claimed in claim 1, wherein only phase differences between adjacent voxels that are less than a second threshold value which is smaller than 180 degrees are taken into account when determining the homogeneity information.

7. The method as claimed in claim 1, wherein shim settings are determined from the homogeneity information and a shim facility is actuated according to the shim settings in the case of an additional magnetic resonance image recording.

8. The method as claimed in claim 1, wherein the determining the attenuation map includes segmenting additional tissue types based on a tissue atlas.

9. The method as claimed in claim 1, wherein the method is for determining an attenuation map for use in positron emission tomography and for use of homogeneity information relating to the magnetic resonance magnetic field for the purpose of determining shim settings, within the framework of a single magnetic resonance image recording.

10. The method as claimed in claim 1, wherein the determining of the attenuation map from fat/water ratios obtained from the image data records is done by way of a 2-point Dixon technology.

11. The method as claimed in claim 2, further comprising:
   calculating a third image data record for the non-excluded voxels by multiplying signal intensities of the first or second image data records with the complex conjugates of signal intensities of the other second or first image data record.

12. The method as claimed in claim 1, wherein phase differences of adjacent voxels are determined as a phase difference map for at least one of the first and second image data records.

13. The method as claimed in claim 3, wherein phase differences of adjacent voxels are determined as a phase difference map for the third image data record.

14. The method as claimed in claim 11, wherein phase differences of adjacent voxels are determined as a phase difference map for the third image data record.

15. The method as claimed in claim 12, wherein the phase difference map is fitted to spherical function phase difference maps.

16. The method as claimed in claim 13, wherein the phase difference map is fitted to spherical function phase difference maps.

17. The method as claimed in claim 14, wherein the phase difference map is fitted to spherical function phase difference maps.

18. The method as claimed in claim 2, wherein shim settings are determined from the homogeneity information and a shim facility is actuated according to the shim settings in the case of an additional magnetic resonance image recording.

19. The method as claimed in claim 2, wherein the determining the attenuation map includes segmenting additional tissue types based on a tissue atlas.

20. A non-transitory computer readable medium including program segments for, when executed on a computer device, causing the computer device to implement the method of claim 1.

* * * * *